(12) United States Patent
Zhang et al.

(10) Patent No.: US 7,931,201 B2
(45) Date of Patent: Apr. 26, 2011

(54) SAMPLE PLATE FOR SUPPORTING BAR CODE SCANNING

(75) Inventors: Peng Zhang, Shenzhen (CN); Jiaofeng Liu, Shenzhen (CN); Baozhen Nie, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 812 days.

(21) Appl. No.: 11/924,445

(22) Filed: Oct. 25, 2007

(65) Prior Publication Data

US 2008/0099564 A1  May 1, 2008

(30) Foreign Application Priority Data

Oct. 26, 2006  (CN) .......................... 2006 2 0015430

(51) Int. Cl.
*G06K 13/04* (2006.01)

(52) U.S. Cl. .................. 235/479; 235/379; 235/462.01; 235/462.14; 235/462.41; 235/462.43; 422/65; 435/288.3; 435/288.7

(58) Field of Classification Search .............. 235/462.01, 235/462.14, 462.41, 462.43, 479; 422/65; 435/288.3, 288.7
See application file for complete search history.

(56) References Cited

U.S. PATENT DOCUMENTS

| | | | |
|---|---|---|---|
| 5,979,761 A | | 11/1999 | Wurz et al. |
| 6,167,767 B1 * | | 1/2001 | Mengel et al. ............. 73/863.21 |
| 2002/0085959 A1 * | | 7/2002 | Carey et al. ................... 422/102 |
| 2006/0210435 A1 * | | 9/2006 | Alavie et al. .................... 422/65 |

FOREIGN PATENT DOCUMENTS

| | | |
|---|---|---|
| CN | 1204816 | 1/1999 |
| JP | 09231299 | 9/1997 |
| JP | 2000099618 | 4/2000 |

OTHER PUBLICATIONS

China patent application No. 200620015430.1, Search Report dated Aug. 8, 2007.
China patent publication No. CN2354186, "Angel-adjustable bar-code scanner", published Dec. 15, 1999. No English translation available.
China patent publication No. CN2153828, "Bar-code through scanner", published Jan. 19, 1994. No English translation available.

* cited by examiner

*Primary Examiner* — Daniel A Hess
*Assistant Examiner* — Michael Andler
(74) *Attorney, Agent, or Firm* — Kory D. Christensen; Stoel Rives LLP

(57) ABSTRACT

A sample plate for supporting bar code scanning is provided, comprising first-circle sample slots distributed along the circumference of the sample plate and clear slots each communicating correspondingly with each of the sample slots, wherein an angle α is formed between the line connecting the center of the circle of each first-circle sample slot to that of the sample plate and the axis of the corresponding clear slot, and the range of α is 4°<α<8°. As an angle is formed between the direction of the axis of the clear slot and that of the diameter of the sample plate, it is able to guarantee a reasonable range of the incident angle when the bar code scanning light is projected on the surface of the bar code.

12 Claims, 3 Drawing Sheets

SAMPLE PLATE FOR SUPPORTING BAR CODE SCANNING

STATEMENT OF RELATED APPLICATION

The present application claims priority of the Chinese Patent Application No. 200620015430.1, entitled "Sample Plate Structure for Supporting Bar Code Scanning", filed on Oct. 26, 2006, which is incorporated herein by reference in its entirety.

FIELD OF THE INVENTION

The present invention relates to a sample plate for supporting bar code scanning, specifically to a configuration of sample slots and corresponding clear slots on the sample plate for supporting bar code scanning.

BACKGROUND OF THE INVENTION

In a full automatic biochemical analyzer, a sample plate is used to carry a variety of test tubes which hold samples, and rotates intermittently according to a predetermined program to transmit the test tubes which hold the samples to positions where the samples are to be extracted such that sampling needles extract the samples. During rotation of the sample plate, a bar code scanner reads sample information under control of the program. Therefore, it is required to adopt a sample plate for supporting bar code scanning. The existing sample plate are provided with sample slots distributed uniformly along the circumference thereof and clear slots for allowing bar code scanning light to pass, in which the clear slot communicates with the sample slot and the axis of the clear slot passes through the center of the circle of the corresponding sample slot and that of the sample plate, thereby causing an unreasonable incident angle in which the bar code scanning light is projected on the bar code on the test tube.

SUMMARY OF THE INVENTION

The technical problem to be solved in the present invention is to overcome the shortcomings in the prior art and there is provided a sample plate which guarantees the reasonable incident angle of the bar code scanning light.

According to an embodiment of the present invention, there is provided a sample plate for supporting bar code scanning, comprising: several first-circle sample slots distributed along the circumference of the sample plate, and several clear slots each of which are correspondingly communicated with each of the first-circle sample slots respectively, wherein an angle α is formed between the line connecting the center of the circle of each first-circle sample slot to that of the sample plate and the axis of the corresponding clear slot.

Preferably, the range of the angle α is: 4°<α<8°. The several first-circle sample slots are distributed uniformly along the circumference of the sample plate.

Each of the clear slots correspondingly communicating with each of the first-circle sample slots is opened towards the exterior margin of the sample plate.

The sample plate for supporting bar code scanning according to the embodiment of the present invention further comprises: several second-circle sample slots which are arranged in the inner side of the first-circle sample slots and distributed along the circumference; and a barrier rib for blocking light, which is disposed between the first-circle sample slots and the second-circle sample slots. Preferably, the second-circle sample slots are distributed uniformly along the circumference of the sample plate.

The sample plate for supporting bar code scanning according to the embodiment of the present invention further comprises: several third-circle sample slots which are arranged between the first-circle sample slots and the barrier rib and distributed along the circumference; and several clear slots each of which correspondingly communicates with each of the third-circle sample slot respectively; wherein the first-circle and the third-circle sample slots are interlaced and an angle α is formed between the line connecting the center of the circle of each third-circle sample slot to that of the sample plate and the axis of the corresponding clear slot. Preferably, the range of the angle α is 4°<α<8°. Still preferably, the several third-circle sample slots are distributed uniformly along the circumference of the sample plate. Each of the clear slots correspondingly communicating with each of the third-circle sample slot passes through the space between the first-circle sample slots and is opened towards the exterior margin of the sample plate.

Preferably, the first-circle, second-circle and third-circle sample slots are shaped as circular concave holes.

The beneficial effect of the present invention is to be able to guarantee a reasonable range of the incident angle when the bar code scanning light is projected on the surface of the bar code on the ground that an angle is formed between the axis of the clear slot and the radial direction of the sample plate.

DETAILED DESCRIPTION OF THE INVENTION

Figure 1:
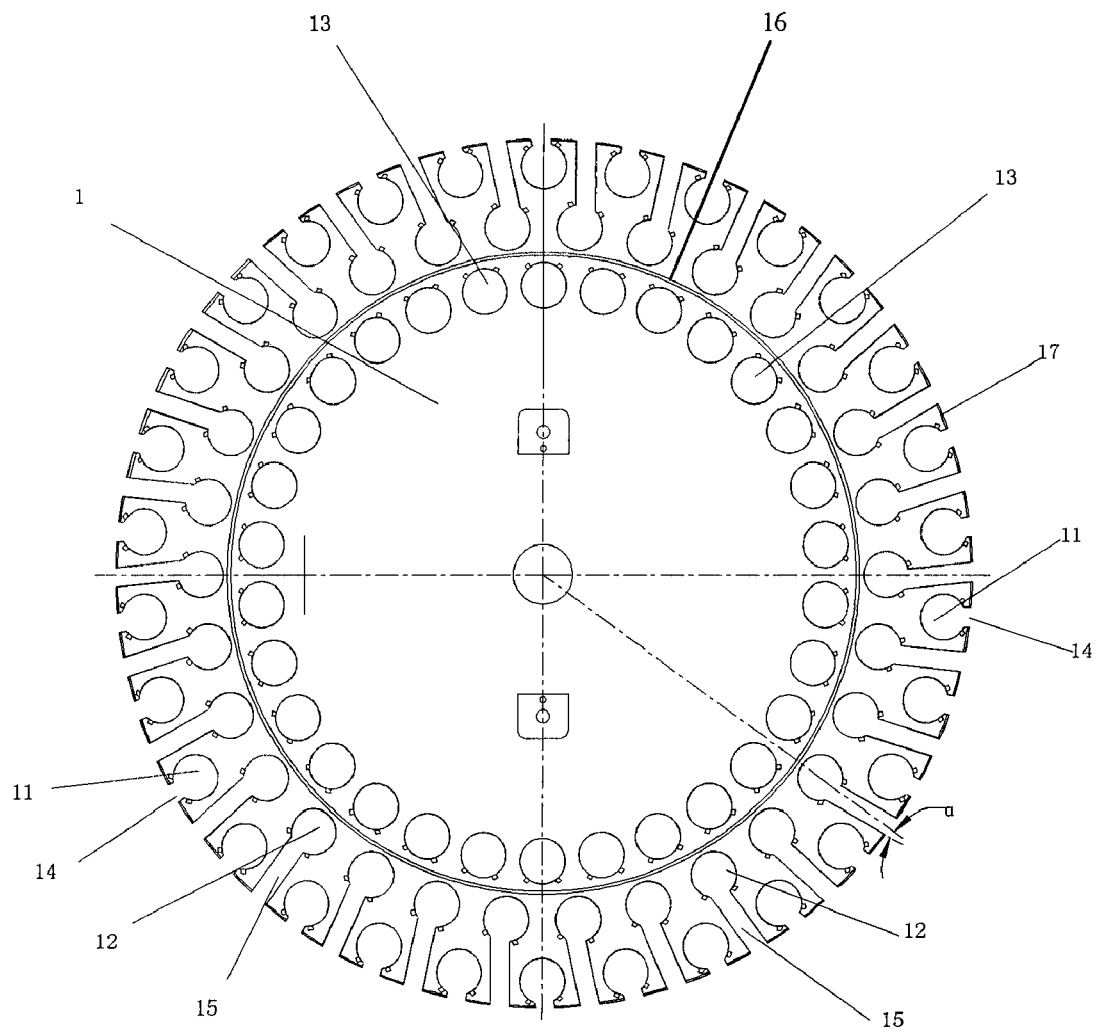
FIG. 1 is a front view of a sample plate for supporting bar code scanning according to the embodiment of the present invention.
Figure 2:
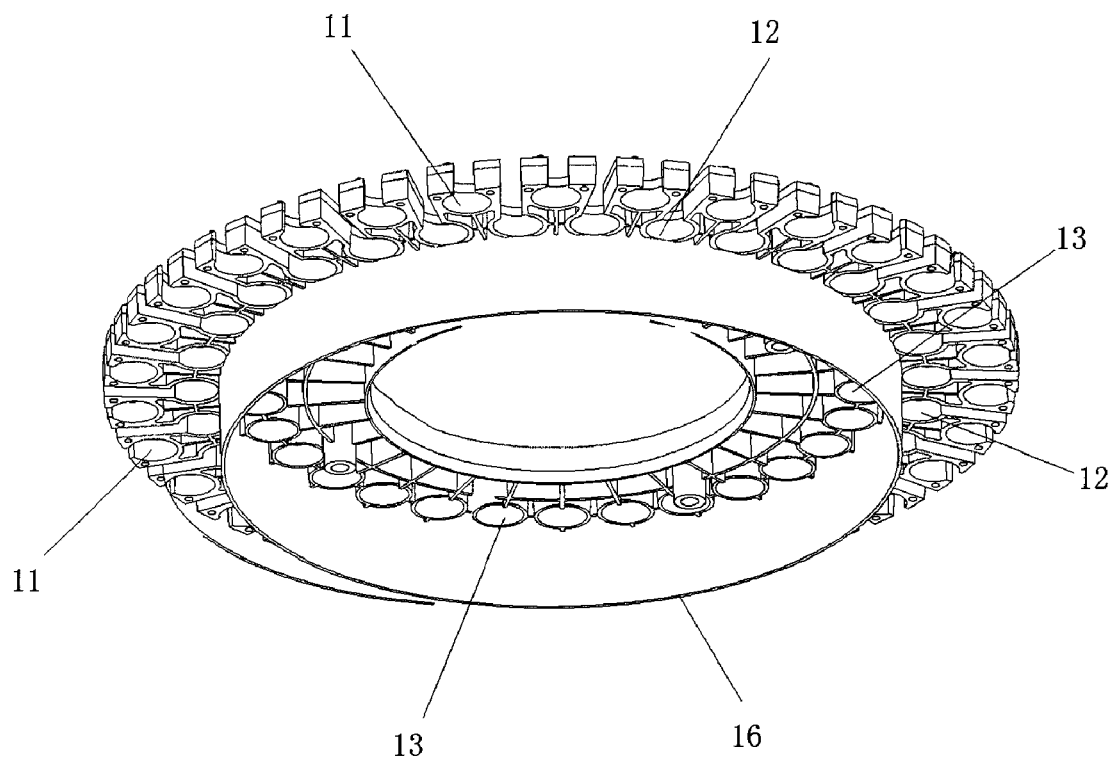
FIG. 2 is a perspective view of a sample plate for supporting bar code scanning according to the embodiment of the present invention.

Referring to FIGS. 1 and 2, a sample plate 1 for supporting bar code scanning according to the embodiment of the present invention has ninety sample slots 11, 12 and 13 for carrying a variety of test tubes which hold samples. The ninety sample slots are divided into an inner circle, a middle circle and an outer circle along the radial direction, each of which is provided with thirty sample slots, wherein the sample slots in the inner circle are used for scaling and emergency treatment, and those in the middle and outer circles are used for conventional detection. Besides, the sample slots in the middle and outer circles support bar code information scanning, whereas those in the inner circle do not. The sample slots 11, 12 and 13 can be in a variety of shapes, but in this embodiment, they are preferably shaped as circular concave holes.

Figure 3:
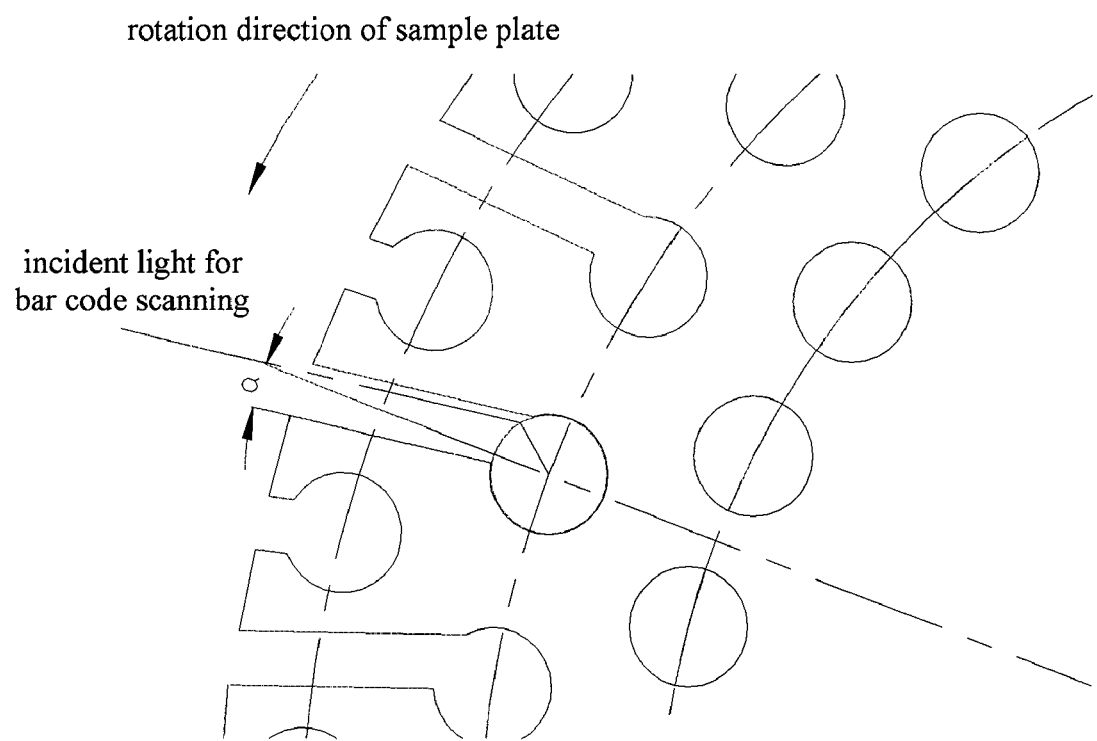
FIG. 3 shows an angle formed between the axis of a clear slot correspondingly communicating with one of third-circle sample slots and the radial direction of the sample plate.

The sample slots 11 and 12 in the outer and middle circles are arranged alternately. Along the circumference 17 of the sample plate 1 are provided with sixty clear slots 14 and 15 distributed uniformly, through which the scanning light for bar code can pass. The sixty clear slots 14 and 15 correspondingly communicate one-to-one with the sixty sample slots 11 and 12 in the outer and middle circles, wherein the clear slots 14 are opened towards the exterior margin of the sample plate 1, and the clear slots 15 communicating with the sample slots 12 pass through the space between the sample slots 11 and are also opened towards the exterior margin of the sample plate 1. In order to guarantee a reasonable range of the incident angle when the bar code scanning light is projected on the surface of the bar code on the test tube, a certain angle α is formed between the line connecting the center of the circle of the sample plate 1 to that of respective sample slots 11 and 12 in the outer and middle circles (i.e. the radial direction of the sample plate 1) and the axis of each of corresponding clear slots 14 and 15 (the axis of the clear slot is parallel to its wall), as shown in FIGS. 1 and 3 respectively. The reasonable range of the angle α is 4°<α<8.

As sample slots 13 in the inner circle do not support bar code information scanning, a barrier rib 16 is provided between the sample slots 13 in the inner circle and the sample slots 12 in the middle circle to prevent mistaken reading of the bar code information on test tubes in the inner circle when the middle and outer circles are scanned.

In virtue of the structure of the sample plate according to the present embodiment, a manufacturing technique of injection molding is employed so as to reduce the cost of parts.

The present invention has been described in detail by way of above-mentioned specific preferred embodiments, but the present invention is not construed to be limited to the embodiments described herein. For a person skilled in the art, some simple inference or substitution can be made without departing from the conception of the present invention, which should be within the protective scope of the present invention.

The invention claimed is:

1. A plate for supporting bar code scanning of test tubes disposed in a plurality of receptacles in the plate, comprising:
    a plurality of first-circle receptacles distributed along a circumference of the sample plate; and
    a plurality of clear slots for receiving a projected bar code scanning light, each clear slot corresponding with one of the first-circle receptacles,
    wherein an angle α is formed between a line connecting a center of each first-circle receptacle to a center of the sample plate and an axis of the corresponding clear slot,
    wherein the line does not intersect a wall of the corresponding clear slot to thereby guarantee that a bar code scanning light projected along the line is incident at the angle α on a barcode when a test tube having the bar code is located in the corresponding first-circle receptacle, and
    wherein the range of the angle α is 4°<α<8°.

2. The sample plate according to claim 1, wherein the first-circle receptacles are distributed uniformly along the circumference of the sample plate.

3. The sample plate according to claim 1, wherein the clear slot corresponding with each first-circle receptacle is opened towards an exterior margin of the sample plate.

4. The sample plate according to claim 1, wherein the first-circle receptacles are shaped as circular concave holes.

5. The sample plate according to claim 1, further comprising:
    a plurality of second-circle receptacles being arranged in a first inner circle between the first-circle receptacles and the center of the sample plate; and
    a barrier rib for blocking the projected scanning light and arranged between the first-circle receptacles and the second-circle receptacles.

6. The sample plate according to claim 5, wherein the second-circle receptacles are distributed uniformly along the first inner circle of the sample plate.

7. The sample plate according to claim 5, wherein the sample plate comprises a top surface and a bottom surface, and wherein the barrier rib forms a second inner circle extending below the bottom surface between the first-circle receptacles and the second-circle receptacles.

8. The sample plate according to claim 5, further comprising:
    a plurality of third-circle receptacles being arranged between the first-circle receptacles and the barrier rib; and
    a plurality of inner clear slots for receiving the projected bar code scanning light, each inner clear slot corresponding with one of the third-circle receptacles,
    wherein the first-circle and third-circle receptacles are interlaced and an angle α is formed between a line connecting a center of each third-circle receptacle to the center of the sample plate and an axis of the corresponding inner clear slot.

9. The sample plate according to claim 8, wherein the line does not intersect a wall of the corresponding inner clear slot to thereby guarantee that a bar code scanning light projected along the line is incident at the angle α on a barcode when a test tube having the bar code is located in the corresponding third-circle receptacle, and
    wherein the range of the angle α is 4°<α<8°.

10. The sample plate according to claim 8, wherein the third-circle receptacles are distributed uniformly.

11. The sample plate according to claim 8, wherein each inner clear slot passes through a space between the first-circle receptacles and is opened towards the exterior margin of the sample plate.

12. The sample plate according to claim 8, wherein the second-circle and third-circle receptacles are shaped as circular concave holes.

* * * * *